(12) United States Patent  (10) Patent No.: US 7,663,107 B2
Taday  (45) Date of Patent: Feb. 16, 2010

(54) METHOD AND APPARATUS FOR QUANTITATIVE ANALYSIS USING TERAHERTZ RADIATION

(75) Inventor: Philip F. Taday, Cambridge (GB)

(73) Assignee: TeraView Limited, Cambridge (GB)

( * ) Notice: Subject to any disclaimer, the term of this patent is extended or adjusted under 35 U.S.C. 154(b) by 0 days.

(21) Appl. No.: 10/559,107

(22) PCT Filed: May 24, 2004

(86) PCT No.: PCT/GB2004/002225

§ 371 (c)(1),
(2), (4) Date: Apr. 19, 2004

(87) PCT Pub. No.: WO2004/106905

PCT Pub. Date: Dec. 9, 2004

(65) Prior Publication Data

US 2006/0237650 A1 Oct. 26, 2006

(30) Foreign Application Priority Data

Jun. 2, 2003 (GB) ................................. 0312627.3

(51) Int. Cl.
G01J 5/02 (2006.01)
(52) U.S. Cl. ................................. 250/339.11
(58) Field of Classification Search ............. 250/339.11
See application file for complete search history.

(56) References Cited

U.S. PATENT DOCUMENTS 5,939,721 A * 8/1999 Jacobsen et al. ............. 250/330
6,335,625 B1 * 1/2002 Bryant et al. ............... 324/637
2002/0005961 A1 1/2002 Netz et al.
2002/0067480 A1 * 6/2002 Takahashi .................... 356/317
2002/0109094 A1 * 8/2002 Goetz et al. ............. 250/339.11
2003/0178584 A1 * 9/2003 Arnone et al. ........... 250/495.1
2004/0126072 A1 * 7/2004 Hoon Lee et al. ........... 385/122

FOREIGN PATENT DOCUMENTS

| EP | 0 841 548 A2 | 5/1998 |
|---|---|---|
| GB | 2 360 842 | 10/2001 |
| GB | 2 372 929 | 9/2002 |
| GB | 2 380 920 A | 4/2003 |
| GB | 2 385 415 | 8/2003 |
| WO | WO 02/095373 | 11/2002 |

OTHER PUBLICATIONS

Rønne, C., Jensby, K., Madsen, G.K.H., Nielsen, O.F., Keiding, S.R., "THz time domain spectroscopy of liquids." SPIE Proceedings 3828 (1999), pp. 266-275.*
J Mullins, "Forbidden Zone," *New Scientist*, vol. 175, No. 2360, Sep. 14, 2003, p. 34.

* cited by examiner

*Primary Examiner*—David P Porta
*Assistant Examiner*—Jessica L Eley
(74) *Attorney, Agent, or Firm*—Dickstein Shapiro LLP

(57) ABSTRACT

A method of quantitatively analysing a sample, the method comprising: irradiating the sample with radiation having a plurality of frequencies in the range from 25 GHz to 100 THz; detecting radiation reflected from and/or transmitted by said sample to obtain a frequency domain waveform of said sample; identifying at least one section of interest of said frequency domain wave-form containing spectral features due to intermolecular or other non-intramolecular excitations; and obtaining a value related to the concentration of a component of the sample from the said section.

29 Claims, 18 Drawing Sheets

METHOD AND APPARATUS FOR QUANTITATIVE ANALYSIS USING TERAHERTZ RADIATION

The present invention relates to an analysis method and/or apparatus which uses radiation in the range from 20 GHz to 100 THz in order to obtain information concerning the concentration of various components of a sample. More particularly radiation in the frequency range from 50 GHz to 84 THz is used, especially that in the range from 100 GHz to 50 THz. The above frequency ranges are colloquially referred to as Terahertz radiation.

Recently, chemometric techniques have allowed the concentration of components of a sample to be derived from a spectrum of the sample. Such techniques have concentrated on analysing spectra which arise due to intramolecular excitations in a sample, for example, so-called near infra ref (NIR) spectra. It has been found that the concentration of a component of a sample may be determined by using the Beer-Lambert Law which states:

$$A_\lambda = \epsilon_\lambda bC$$

where $A_\lambda$ is the absorption as a function of frequency, $\epsilon_\lambda$ is absorptivity coefficient, b is the pathlength through the sample and C is the concentration.

Where the sample has more than one component, the Beer Lambert law states that the contribution from the two components adds linearly, thus for a two component sample:

$$A_\lambda = \epsilon_{1\lambda} bC_1 + \epsilon_{2\lambda} bC_2$$

The suffixes '1' and '2' denote the first component and the second component respectively. The concentration C and the path length b will remain fixed for all wavelengths and the absorption and the absorption coefficient will vary for different wavelengths. Thus, in a simplified model, by measuring the absorption at various wavelengths it is possible to establish the concentrations of the first and second components. This method has previously been used to determine the concentration of a molecule in a sample by studying the part of the spectra where features due to the excitation of intramolecular bonds are observed.

The inventors of the present invention have surprisingly found that chemometric techniques may also be used to derive concentration data from spectral features which arise from non-intramolecular excitations such as intermolecular excitations etc. Intermolecular excitations arise due to interactions between neighbouring molecules as opposed to excitations within the molecules themselves. Therefore, it is surprising that these complex intermolecular interactions can give a reliable indication of the concentration of a component of a sample. Further, other types of non-intramolecular excitations may be used such as rotational excitations and have been found of particular use when studying vapour.

Thus, in a first aspect, the present invention provides a method of quantitatively analysing a sample, the method comprising:

irradiating the sample with radiation having a plurality of frequencies in the range from 25 GHz to 100 THz;

detecting radiation reflected from and/or transmitted by said sample to obtain a frequency domain waveform of said sample;

identifying at least one section of interest of said frequency domain waveform containing spectral features due to intermolecular excitations or other non-intramolecular excitations; and obtaining a value related to the concentration of a component of the sample from the said section.

Intermolecular excitations which give rise to these spectral features may be excitations between individual molecules or excitations in the large scale crystalline or polycrystalline structure including phonon vibrations. Non-intramolecular excitations such as rotational excitations may also be used and are of particular use when analysing vapour.

To excite the above excitations, preferably radiation in the range from 100 GHz to 5 THz is used.

The present invention may be used with any type of sample, for example, it may be used to determine the relative concentrations of two or more components of a sample, the two or more components may be completely different molecules or may be polymorphs or psuedo polymorphs of the same molecule.

Polymorphs or allotropes are the names given to different crystallographic arrangements of the same elements or molecules. A classic example of two polymorphs or allotropes is that of graphite and diamond which are both polymorphs of carbon. Graphite and carbon have different mechanical, electrical and chemical properties and are easily distinguishable from their physical appearances.

Previously, the inventors have shown that by identifying the features of a spectrum which arise due to non intramolecular excitations such as intermolecular excitations, it is possible to be able to distinguish between two or more polymorphs or psuedo polymorphic states of a molecule within a sample. The inventors have found that by performing a chemometric analysis of the characteristics of a spectrum which are due to non intramolecular excitations such as intermolecular excitations, it is possible to be able to determine the amount of one polymorph in a sample relative to the amount of another polymorph or psuedo polymorph of the same molecule. Thus, the sample may comprise a molecule which can form at least two polymorphs or psuedo polymorphic states.

When analysing a sample with two or more polymorphs of the same molecule, preferably the at least one section of interest is chosen to be a region where the two or more polymorphs differ.

Examples of pharmaceutical compounds which either exhibit or are expected to exhibit polymorphs are: AG-337, Ampicillin, Androstanolone, Aspartme, Benoxaprofen, Captopril, Carbamazepine anhydrate, Carbamazepine dihydrate, Carbovir, Cefaclor dihydrate, Cefamandole nafate, Cefazolin, Cefepime.2HCl, Chlorpropamide, Cimetidine, Compound H, Cortisone acetate, Cyclopenthiazide, Delavirdine mesylate, Diflunisal, 1,2-Dihydro-6-neopentyl-2-oxonicotinic, 11-α-Dimethyl-3-hydroxy-4pyridone, Diphenhdramine HCl, Dirithromycin, Disodium clodronate, DuP 747, Erthtrocin, β-Estradiol, Fluconazole, Flucinolone acetonide, p-Formyl-trans-cinnamic acid, Fosinopril sodium, Frusemide, Glburide, Glycine, Griseofulvin, Idomethacin, L-660,71, Lactose, Losartan, Lufenuron, Mefloquine HCl, 4'-Methyl-2'-nitroacetanilide, 5-Methyl-2-{(2-nitrophenyl)amino}-3-thiopheneccarbonitrile, MK-571, MK-679, Mofebutazone, Nabilione, Nedocromil magnesium, Neotame, Nicardipine HCl, Nimodipine, Oxyphenbutazone, Paracetamol, Paroxetine HCl, Phenylbutazone, Prednisolone tert.-butylacetate, Ranitidine HCl, RG-12525, Salbutamol, SC-25469, SC-41930, Spironolactone, SQ-33600, Sulfainethoxazole, Sulfaproxiline, Sulphanilamide and Testosterone.

As mentioned above, spectral features arising from the non-intramolecular excitations such as intermolecular excitations may also be used to quantitatively determine the concentration of the active component regardless of whether it exhibits polymorphs or not within a tablet. Thus, preferably, the sample is a tablet comprising an active component and at least one excipient.

The sample is not restricted to pharmaceuticals, the above method may also be used to determine the concentrations of components in non-pharmaceutical samples, for example explosives. Semtex H is a mixture of two crystals, RDX and PETN. Such a sample may be analysed to determine the concentration of the components by the same method used for a pharmaceutical sample.

Often, it is desirable to identify sections of interests as regions where there are significant spectral features due to the component to be analysed such as maxima and/or minima.

Over time, the active components in pharmaceuticals may deteriorate for example, phase changes may occur such as a change of polymorphic form. This deterioration is often induced by the environment of the pharmaceutical, for example, air and more specifically water vapour. To prevent such deterioration occurring, pharmaceuticals are often supplied in protective packaging.

When the seal of the package starts to degrade, air and vapour may enter the package. The vapour may thus be monitored using the above method to confirm the integrity of the package. The method may be configured to monitor the concentration of water or other vapour in the package. The method may also be configured to monitor the ingress of any organic or non-organic solvent into the package.

When a pharmaceutical is placed in a package, the pharmaceutical be it in tablet form, capsule form or otherwise, there is usually some free space in the package between the pharmaceutical and the seal. This space is generally referred to as the "headspace".

Preferably, radiation is analysed which has been reflected through or transmitted by said headspace. For analysing the concentration of vapour, preferably features due to rotational excitations are analysed.

It is also possible to analyse the concentration of a pharmaceutical or other sample while it is in its package since the radiation will penetrate the package. Thus, both the sample may be analysed in the package and the integrity of the seal of the package may be checked at the same time.

The radiation may be continuous wave (CW) radiation, but is preferably pulsed radiation.

When the spectra are obtained, the concentration is derived from the spectra. The analysis may use the height of certain peaks in the spectra or may use the area under certain parts of the spectra.

Prior to analysis operations may be performed on the spectra in order to enhance certain characteristics and hence obtain a more accurate concentration measurement.

The inventors have found that it is particularly desirable to take a differential of the spectra when analysing features due to intermolecular excitations or non intramolecular features. Preferably, either the first or second differential are used.

The "baseline" of the spectra may also be removed from the spectra in order to give more accurate concentration readings. The "baseline" or background may be removed by a number of methods such as shifting the spectra so that the minimum on the y-axis is zero. Alternatively, a straight line may be fitted to the spectra which is then subtracted from the spectra. The baseline may also be subtracted by measuring the background signal using a reference sample and subtracting this background signal from the measured data.

The spectra may also be normalised.

In a second aspect, the present invention provides use of radiation having a plurality of frequencies in the range from 25 GHz to 100 THz; to determine the vapour content in a sealed package by:
irradiating the sample with radiation having a plurality of frequencies in the range from 25 GHz to 100 THz;
detecting radiation reflected from and/or transmitted by said package to obtain a frequency domain waveform of said sample;
identifying at least one section of interest of said frequency domain waveform containing spectral features due to intermolecular or other non-intramolecular excitations; and
obtaining a value related to the concentration of vapour content within said package from the said section.

In a third aspect, the present invention provides use of radiation having a plurality of frequencies in the range from 25 GHz to 100 THz; to determine the quantity of a component of a pharmaceutical:
irradiating the sample with radiation having a plurality of frequencies in the range from 25 GHz to 100 THz;
detecting radiation reflected from and/or transmitted by said pharmaceutical to obtain a frequency domain waveform of said sample;
identifying at least one section of interest of said frequency domain waveform containing spectral features due to intermolecular or other non-intramolecular excitations; and
obtaining a value related to the concentration of a component of the pharmaceutical from the said section.

In a fourth aspect, the present invention provides apparatus for quantitatively analysing a sample, comprising:
a source for irradiating the sample with radiation having a plurality of frequencies in the range from 25 GHz to 100 THz;
a detector for detecting radiation reflected from and/or transmitted by said sample to obtain a frequency domain waveform of said sample;
means for identifying at least one section of interest of said frequency domain waveform containing spectral features due to intermolecular excitations or other non-intramolecular excitations; and
means for obtaining a value related to the concentration of a component of the sample from the said section.

The detector may be a direct detector of THz radiation or it may be of the type which converts THz radiation into an easily readable signal.

For example, the detector may comprise a non-linear crystal which is configured such that upon irradiation of a probe beam and a THz beam, the polarisation of the probe beam is rotated. The probe beam can be of a frequency which can be easily measured (for example near infra-red). Typical crystals which exhibit this effect, the so-called "AC Pockels" effect are GaAs, GaSe, $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium). This type of detection mechanism is generally referred to as 'Electro-optic sampling' or EOS.

Alternatively, the detector could be a so-called photoconducting detector. Here, the detector comprises a photoconductive material such as low temperature grown GaAs, Arsenic implanted GaAs or radiation damaged Si on Sapphire. A pair of electrodes, for example in a bow-tie configuration or in a transmission line configuration are provided on a surface of the photoconductive material. When the photoconductive material is irradiated by the reflected radiation and also, the probe beam, a current is generated between the two electrodes. The magnitude of this photovoltage current is an indication of the magnitude of the THz signal.

Although it is possible to generate THz radiation directly, the most effective THz generation can be achieved by converting a pump beam into a THz beam. To do this, the source comprises a frequency conversion member and a source of a pump beam.

The pump beam may be supplied by a Ti:sapphire Yb:Er doped fibre, Cr:LiSAF, Yb:silica, Nd:YLF, Nd:Glass, Nd:YAG, Yb:BOYS, Yb:Phosphate Glass, Yb:GdCOB, Yb:YAG, YbKG d(WO$_4$)$_2$ or Alexandrite laser There are many possible options for the frequency conversion member. For example, the frequency conversion member may comprise a non-linear member, which is configured to emit a beam of emitted radiation in response to irradiation by a pump beam. Preferably, the pump beam comprises at least two frequency components, (or two pump beams having different frequencies are used), the non-linear member can be configured to emit an emitted beam having a frequency which is the difference of the at least two frequencies of the pump beam or beams. Typical non-linear members are: GaAs or Si based semiconductors. More preferably, a crystalline structure is used. The following are flirter examples of possible materials: $NH_4H_2PO_4$, ADP, $KH_2PO_4$, $KH2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, GaSe or organic crystals such as DAST (4-N-methylstilbazolium).

In order to produce an emitted beam having a frequency in the THz regime, preferably the frequencies of the pump beam or beams are between $0.1 \times 10^{12}$ Hz and $5 \times 10^{14}$ Hz.

Alternatively the frequency conversion member is a photoconducting emitter, such an emitter comprises a photoconductive material such as low temperature grown or arsenic implanted GaAs or radiation damaged Si or Sapphire.

Electrodes which may be of any shape such as a dipole arrangement, a double dipole arrangement, a bow-tie arrangement or transmission line arrangement are provided on the surface of the photoconductive material. At least two electrodes are provided. Upon application of a bias between the electrodes and irradiation of a pump beam(s) having at least two different frequency components, a beam of radiation is emitted having a frequency different to that of the at least two frequency components of the pump beam or beams.

P-i-n emitters may also be used as the source. These are photodiodes which are irradiated with a short pulse laser (pulse length approximately 10 fs, wavelength approximately 800 nm). These emitters can emit at frequencies up to 20 THz.

When a pulse having a plurality of frequencies passes via a sample to a detector, the various frequencies will not arrive at the detector at the same time due to the frequency dependent response of the sample. A time domain signal can be established by measuring the amplitude of the detected radiation with respect to time. In order to achieve this, it is preferable if a scanning delay line is inserted into either the path of the probe or pump beam. The delay line can be configured to scan over the whole length of the pulse. This time domain spectrum will be converted to a frequency domain spectrum by fourier transforming the spectrum.

The present invention will now be described with reference to the following preferred non-limiting embodiments in which.

Figure 17:
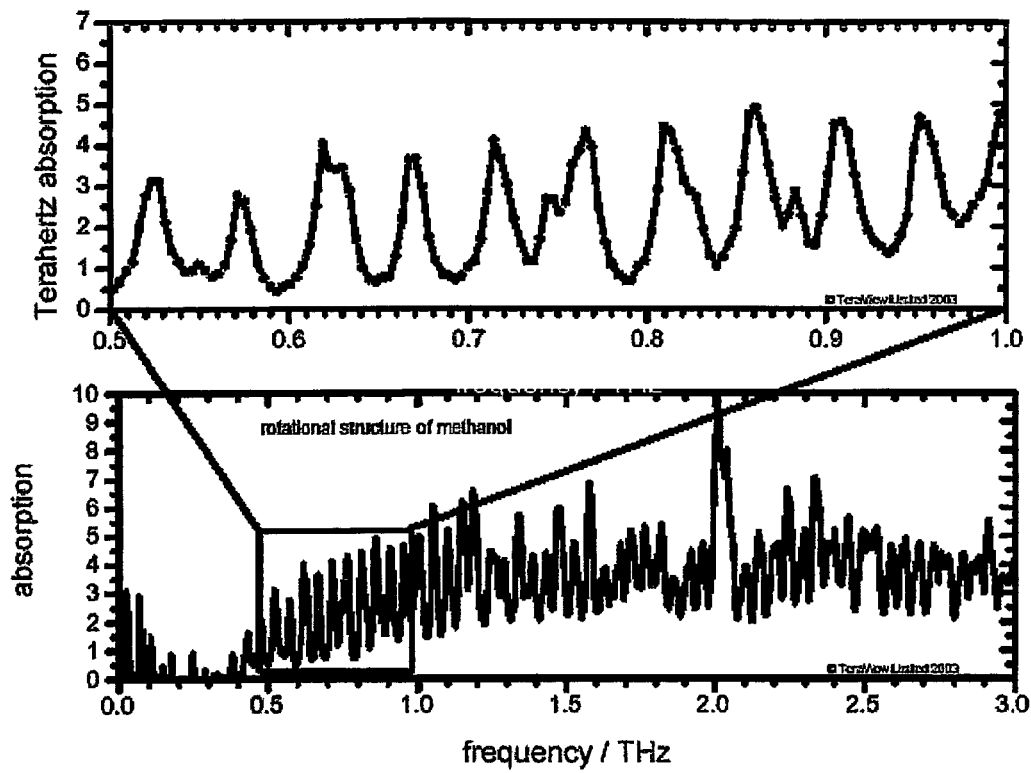
Figure 18:
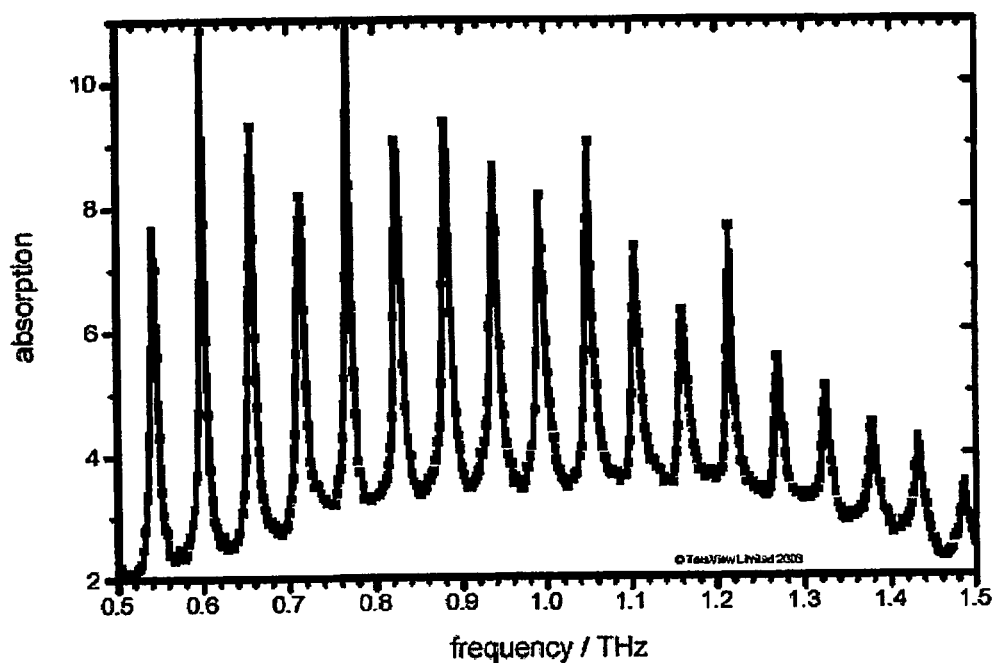
Figure 19:
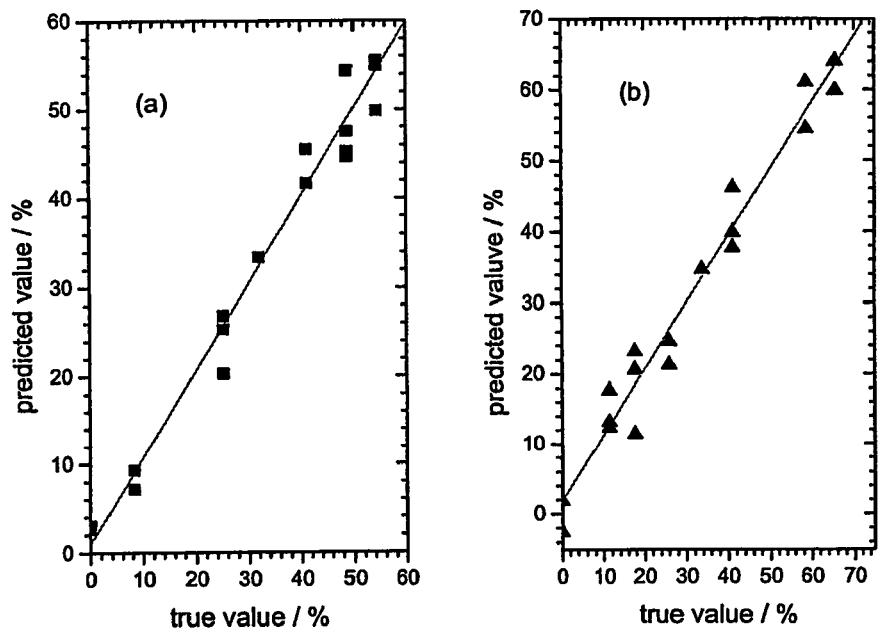
Figure 20:
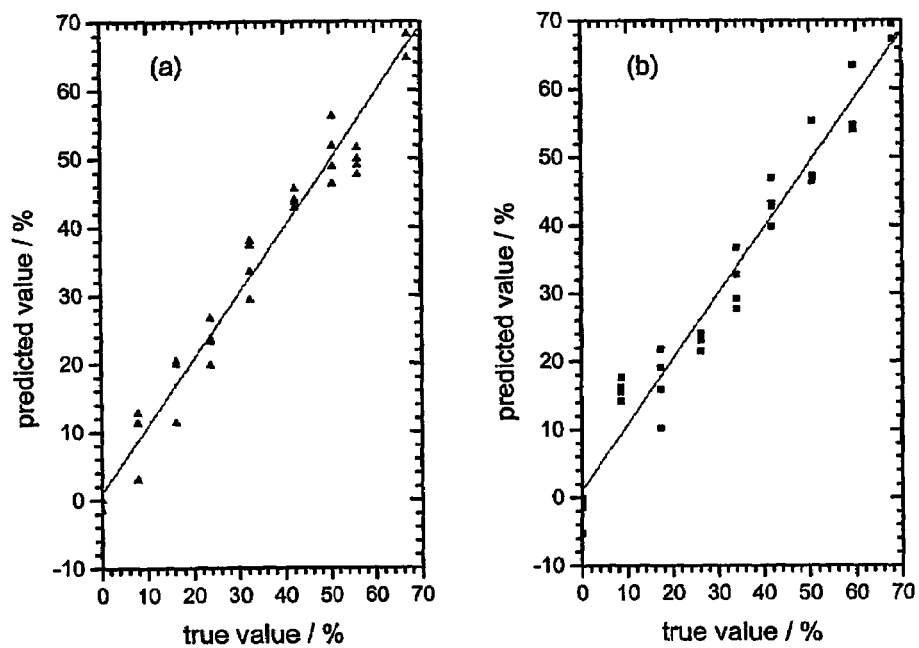

FIG. 17*a* is a plot of the absorption against frequency for methanol and FIG. 17*b* is a section of the plot of 17*a* enlarged;

FIG. 18 is a plot of absorption against frequency for dichloromethane;

FIG. 19*a* is a plot of data from a chemometrics analysis package for acetylsalicyclic acid (aspirin) derived from a plurality of tablets having known aspirin concenrtrations and FIG. 19*b* is a plot of data from a chemometrics analysis package for lactose derived from the same tablets as FIG. 19*a*; and FIG. 20*a* is a plot of data from a chemometrics analysis package for 4-acetamidophenol (paracetamol) derived from a plurality of tablets having known aspirin concenrtrations and FIG. 20*b* is a plot of data from a chemometrics analysis package for lactose derived from the same tablets as FIG. 20*a*.

Figure 1:
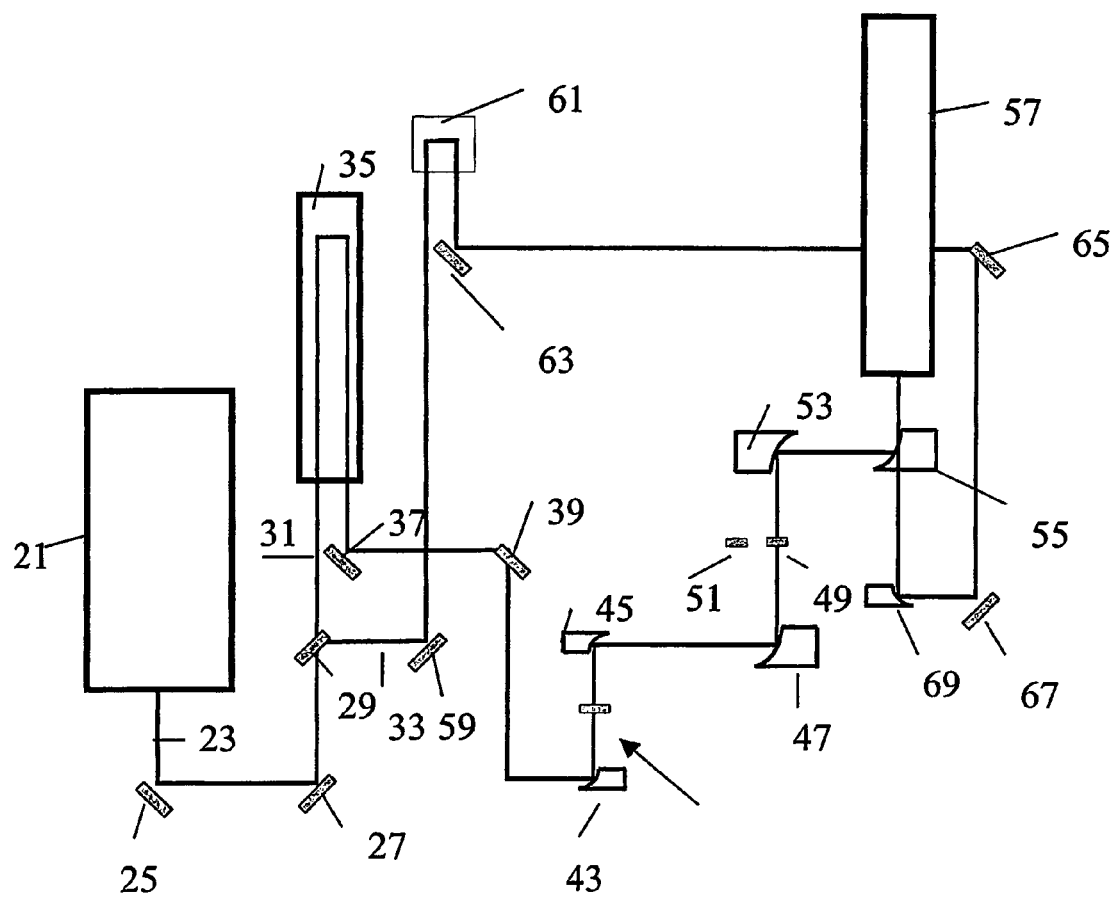
FIG. 1 is a schematic of the apparatus used to measure a spectrum of a sample.

FIG. 1 illustrates an apparatus which can be used to perform the method of the present invention.

The apparatus comprises an ultra-short pulse laser 21 which may be, for example, ati:sapphire Yb:Er doped fibre, Cr:LiSAF, Yb:silica, Nd:YLF, Nd:Glass, Nd:YAG, Yb:BOYS, Yb:Phosphate Glass, Yb:GdCOB, Yb:YAG, YbKG d(WO$_4$)$_2$ or Alexandrite laser. This laser 21 emits pulses of radiation 23 each of which comprise a plurality of frequencies. This pulse is reflected by first mirror 25 and second mirror 27 into beam splitter 29. The beam splitter splits the beam into a pump pulse 31 which is used to irradiate the sample and a probe pulse 33 which is used during detection.

The pump pulse 31 is into first scanning delay line 35. Scanning delay line 37 in its simplest form comprises two mirrors which serve to reflect the beam through a 180°. These mirrors are then quickly swept backwards and forwards in order to vary the path length of the pump pulse 31. The output pump pulse from the first scanning delay line is then directed by mirrors 37 and into parabolic mirror 43.

Parabolic mirror 43 directs the pump pulse onto a source which comprises a frequency conversion member and a bow-tie emitter. The frequency conversion member is configured to mix the incident radiation and output radiation derived from the differences of the input frequencies, so-called difference frequency generation. This technique is described in more detail in GB 2 347 835.

The output is then reflected off second parabolic mirror 45 and onto third parabolic mirror 47 which directs the radiation onto sample 49. The sample may be replaced with a reference sample 51 in order to remove background features from the final results. The radiation which is transmitted through sample 49 is then collected by fourth parabolic mirror 53 and is then combined with the probe beam using combining parabolic mirror 55.

Combining parabolic mirror 55 comprises a parabolic surface with an aperture. The detected radiation is directly collected by parabolic surface, this is combined with the probe beam 33 which is transmitted through the aperture in the parabolic surface. The combined beams are then sent into an electro-optic sampling detection unit 57. The details of this are described in GB 2 347 835.

Prior to recombining with the pump beam 31, the probe beam 33 is directed by mirror 59 into second scanning delay line 61. This operates in the same manner as the first scanning delay line 35. The outputted probe beam 33 is then reflected off first probe beam 63 onto second probe beam mirror 65 and onto third probe beam mirror 67 into probe beam parabolic mirror 69. Parabolic mirror then directs the probe beam into the aperture of recombining parabolic mirror 55 for recombination with the pump beam.

The sample introduces a time delay in the path of the pump pulse. The delay is dependent on both the absorption coefficient and the refractive index of the sample. In order to obtain an EOS detection signal, the frequency component of the probe beam must be in phase with a frequency component of the pump beam. Variation of the first and second scanning delay line allows the phase of the probe beam and/or pump beam to be swept with respect to the pump beam and/or probe beam and thus allows for measurement of the delay time of each frequency component which passes through the sample.

In the apparatus of FIG. 1, the pump beam and probe beams are focussed using parabolic mirrors as opposed to glass lenses. This is because glass lenses disperse the pump beam, probe beam and the produced THz radiation. Thus, it is advantageous to design the system to avoid transmission of the radiation through anything other than the sample.

Figure 2:
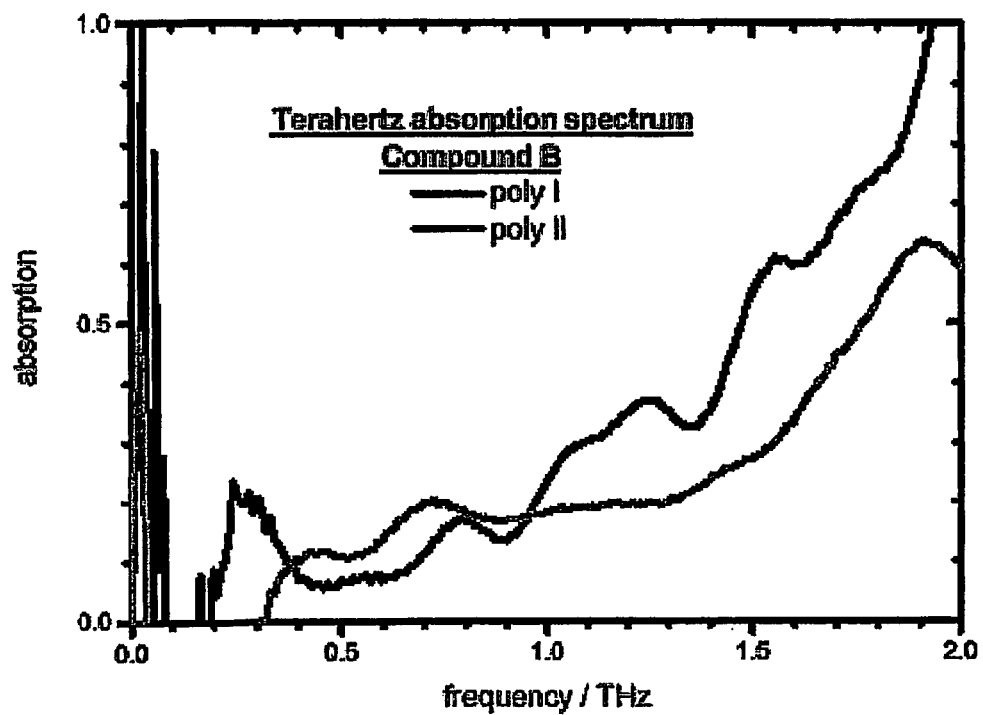
FIG. 2 are spectra constructed by plotting absorption in arbitrary units along the y axis against frequency in Terahertz along the x axis, two spectra are shown, one for Polymorph I of compound "B", the other for Polymorph II of compound "B"

FIG. 2 are spectra constructed by plotting absorption in arbitrary units along the y axis against frequency in Terahertz along the x axis. Two spectra are shown, one for Polymorph I of an unknown compound "B", the other for Polymorph II of compound "B". The trace for polymorph I is the uppermost trace at 2 THz. The data is raw data obtained by using measurement apparatus of the type described with reference to FIG. 1.

The two spectra shown in FIG. 2 illustrate the dramatic differences between the spectra of two polymorphs of the same compound. The differences between these two spectra may then be used to calculate the relative concentrations of the two polymorphs in a tablet.

Figure 3:
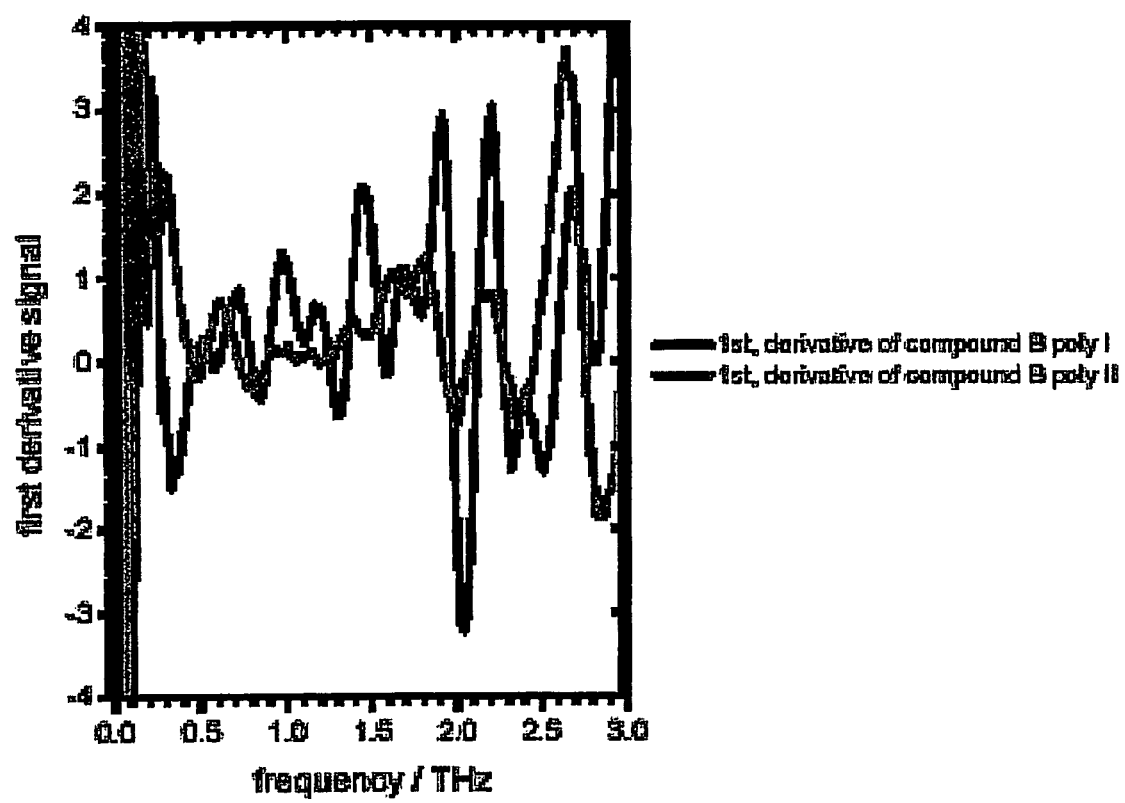
FIG. 3 are plots of the first derivative against frequency for the spectra of polymorphs I and II of FIG. 2.

In accordance with this preferred embodiment, in order to extract quantitative information from the raw spectra of FIG. 2, the two spectra are differentiated as shown in FIG. 3. The differences between the two differentiated spectra are more marked than those between the two raw spectra of FIG. 2.

Figure 4:
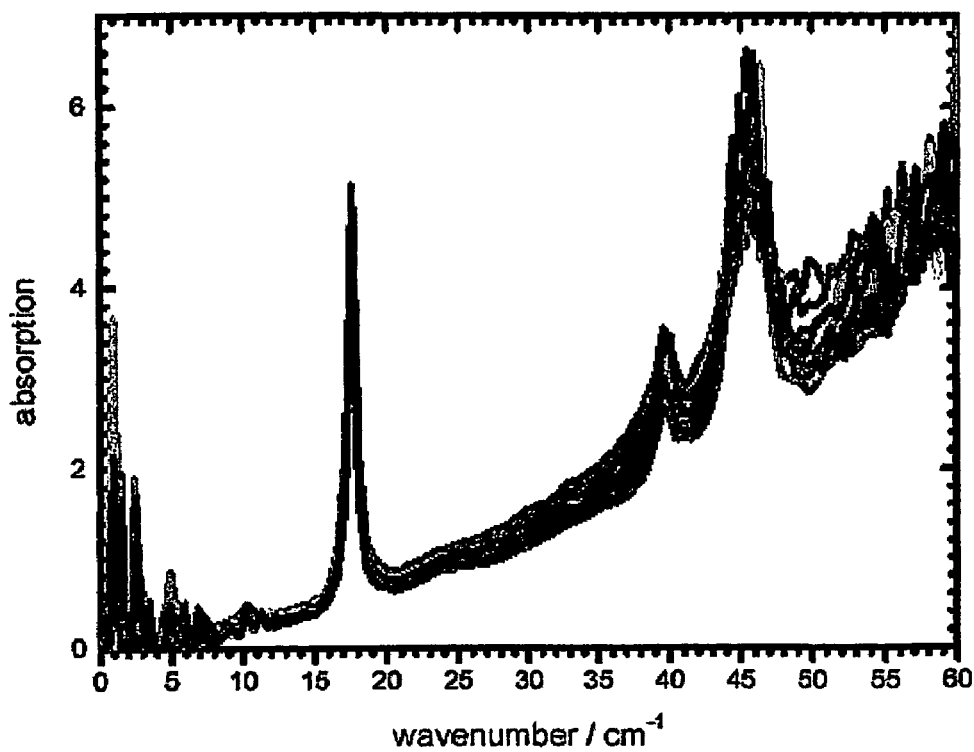
FIG. 4 is a plot of a plurality of spectra constructed by plotting absorption on the y axis against wavenumber (cm$^{-1}$) on the x axis for a plurality of tablets containing a mixture of the two polymorphs of FIGS. 2 and 3 and excipients. The x-axis may be converted to Terahertz by dividing by 33.333.

FIG. 4 is a plot of a plurality of spectra constructed by plotting absorption on the y axis against wavenumber (cm$^{-1}$) on the x axis for a plurality of tablets containing a mixture of the two polymorphs of FIGS. 2 and 3 and excipients. The x-axis may be converted to Terahertz by dividing by 33.333.

The excipients used in the tablets are lactose and cellulose. The spectral features at 0.51 THz (17 cm$^{-1}$), 1.2 THz (40 cm$^{-1}$) and 1.35 THz (45 cm−1) are due to lactose. Cellulose has no strong spectral features in the range shown in the figure.

In order to derive quantitative data about the amount of Polymorphs I and II in the tablets shown in FIG. 4, a chemometric analysis is performed concentrating on the features of the spectrum which arise from intermolecular excitations.

A commercial chemometrics package, OPUS-NT Quant from Bruker Optic GmbH was used to analyse the spectra. The software can derive a single figure representative of a selected frequency range by using the peak heights within the chosen frequency range and/or the area under the curve. A partial least squares fit method is then performed in order to determine a representative quantitative value.

Figure 5:
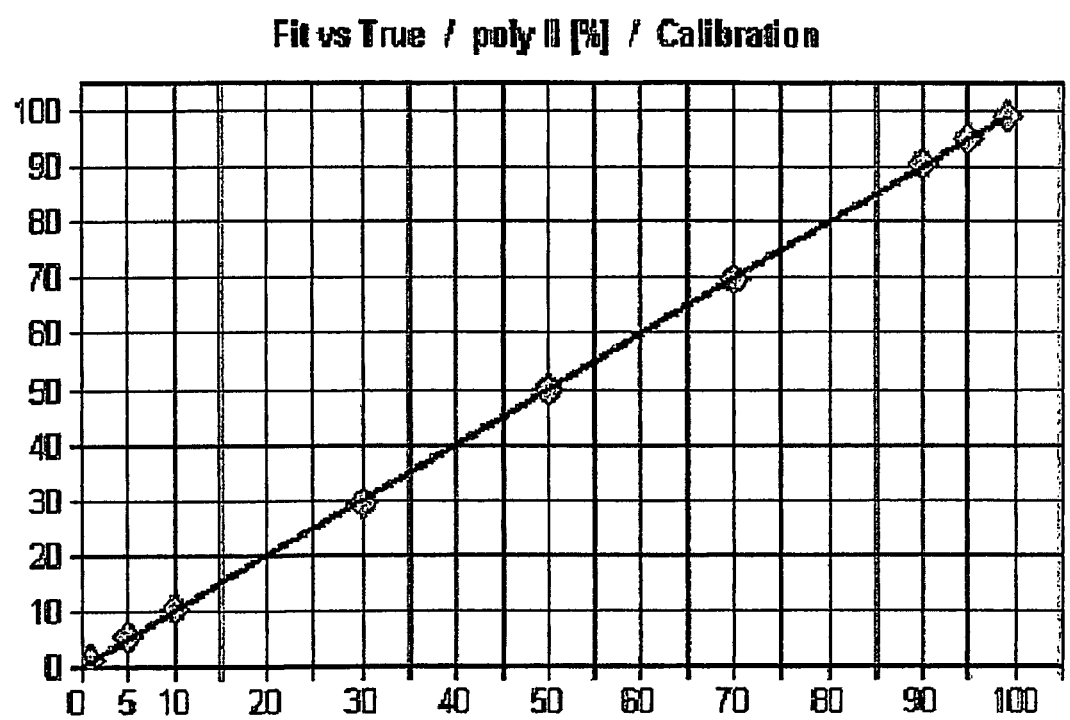
FIG. 5 is a plot of the calibration data for polymorph II calculated using a chemometrics analysis package for a plurality of samples having a known concentration of polymorph II.

First, a calibration plot is constructed by performing a chemometric analysis on samples of known compositions. FIG. 5 is a plot of the calibration data for polymorph II calculated using a chemometrics analysis package for a plurality of samples having a known concentration of polymorph II. The figure derived from each of the spectra is then plotted on the y axis and the true concentration of Polymorph II in each sample is plotted on the x axis to produce a calibration plot. A straight line is then fitted to the data.

To assess the calibration models, the root mean square error of estimation (RMSEE) and the determination coefficient ($R^2$) are calculated. The residual is the difference between the true, $C_{0i}$, and fitted value, $C_i$. Thus the sum of squared errors (sse) is the quadratic summation of these values, i.e.

$$sse = \sum_{i=1}^{N_c} [C_i - C_{0i}]^2$$

The root mean square error of estimation (RMSEE) is calculated then calculated using sse, $N_c$ the number of samples and H the rank or the number of Partial Least Squares (PLS) vectors employed to fit the data.

$$RMSEE = \sqrt{\frac{sse}{N_c - H - 1}}$$

The determination coefficient ($R^2$) gives the percentage of variance present in the true component values, which is reproduced in the regression. $R^2$ approaches 100% as the fitted concentration values approach the true values, $$R^2 = \left(1 - \frac{SSE}{\sum (y_i - y_m)^2}\right) \cdot 100$$

In order to determine the value indicative of the concentration, a frequency range or frequency ranges of the spectra are identified. To produce the calibration plot of FIG. 5, the regions 53.9-49.3 cm$^{-1}$ (1.62-1.48 THz), 36.6-32.2 cm$^{-1}$ (1.09-0.97 THz) and 23.9-19.0 cm$^{-1}$ (0.71-0.57 THz) were analysed from the spectra. As can be seen from FIG. 3, these are spectral regions where there is a large difference in the signature from polymorph I and polymorph II. These are also regions which do not coincide with the strong lactose spectral features demonstrated in FIG. 4.

Figure 6:
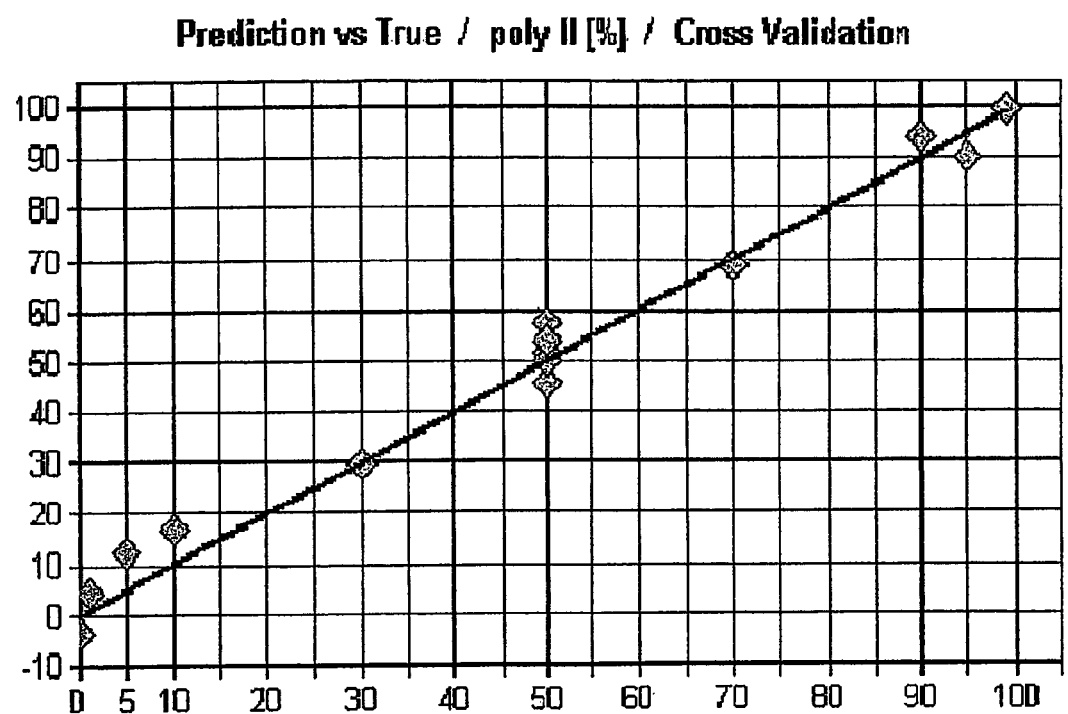
FIG. 6 is a plot of the validation data of the calibration data of FIG. 5 for polymorph II produced using a chemometrics analysis package.

Validation of the calibration plot of FIG. 5 is then performed to demonstrate the accuracy of the calibration plot. Extra samples with a known concentration of Polymorph II are then analysed as described above for the calibration samples and plotted against the calibration data to assess the accuracy of the calibration plot and demonstrate its validity. The validation data is shown in FIG. 6.

Specifically, during the cross validation process, the derived model is tested against the root mean square error of cross-validation, which is defined as $$RMSECV = \sqrt{\frac{\sum_{i=1}^{N_c} (C_i - C_{0i})^2}{N_c}}$$

where $C_i$ and $C_{0i}$ are the predicted and true concentrations of the $i^{th}$ sample of the test set, and $N_c$ is the total number of samples. For the cross-validation test, one spectrum was removed from the dataset and the others used to predict the value of the missing spectrum. A number of different multivariate calibration models were investigated, the rank or the number of PLS vectors employed was varied automatically by the programme used and the spectral range, and the data pre-processing steps.

Figure 7:
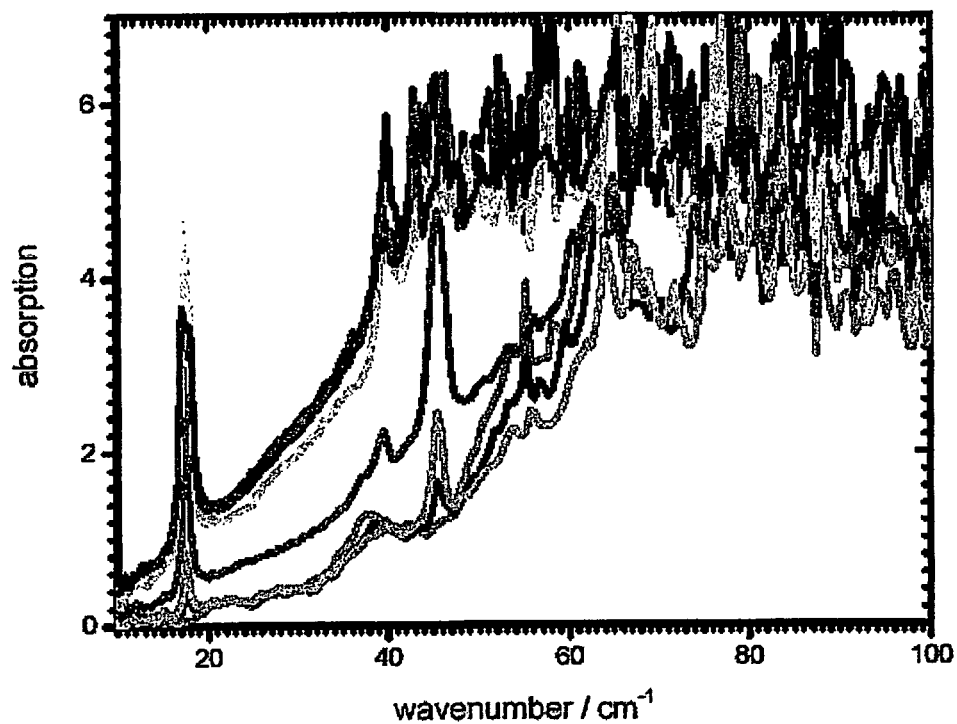
FIG. 7 is a plot of absorption against wavenumber cm$^{-1}$ for a plurality of tablets comprising Polymorph I and excipients.

FIG. 7 is a plot of absorption against wavenumber cm$^{-1}$ for a plurality of tablets comprising Polymorph I and excipients. In order to convert the x-axis to frequency in THz it is necessary to divide by 33.333.

In the spectrum of FIG. 7, the percentage of polymorph I in the tablets was varied between 0% and 100%. The excipient concentration was varied accordingly. The excipients used were lactose and cellulose. The features at 0.51 THz (17 cm$^{-1}$), 1.2 THz (40 cm$^{-1}$) and 1.35 THz (45 cm$^{-1}$) are due to lactose. Cellulose has no strong absorption features in this range.

Figure 8:
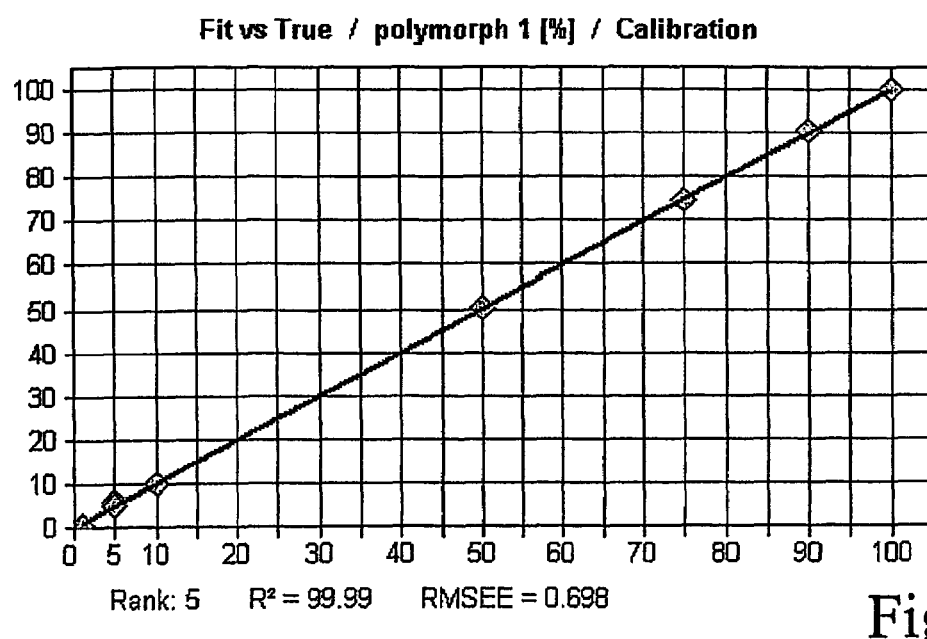
FIG. 8 is a plot of calibration data from a chemometrics analysis package for Polymorph I derived from a plurality of samples of Polymorph I of known concentration.

FIG. 8 is a plot of calibration data for Polymorph I obtained from the spectrum of FIG. 7. The data is processed in a similar manner to that described with reference to FIG. 5. The first derivative of the spectrum is taken over the range 39.06-13.67 cm$^{-1}$ (1.17-0.41 THz).

Figure 9:
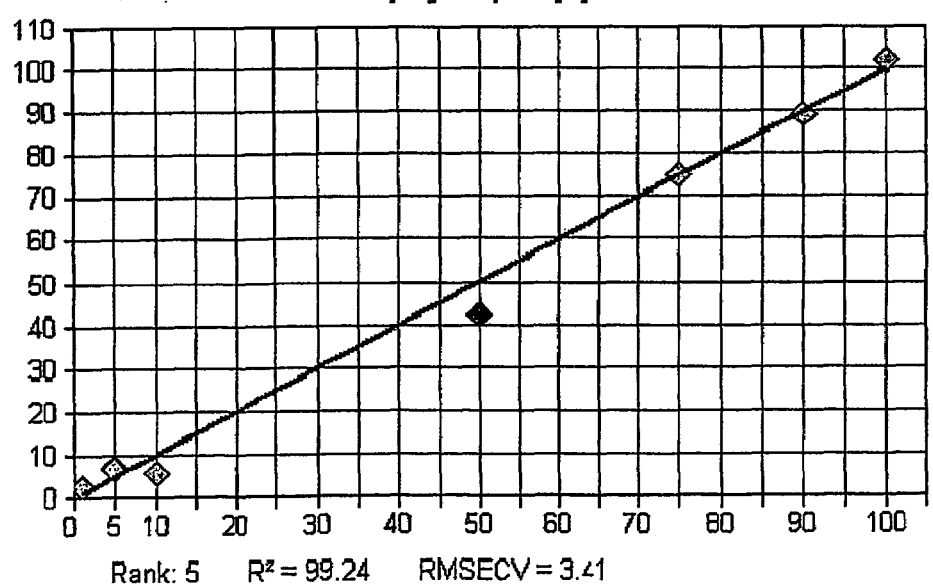
FIG. 9 is a plot showing the validation of the calibration plot of FIG. 8.

FIG. 9 illustrates validation of the calibration plot of FIG. 8. It can be seen that accurate data is illustrated for concentrations of 5% and less. Today, drug substances are becoming more potent resulting in low dose tablets where the drug represents only a small percentage of the total formulation. Thus, FIG. 9 clearly illustrates that the method of the present invention can be used to reliably detect the amount of drug in low dosage tablets.

In addition to determining the concentration of active components such as Polymorph I, the spectrum may also be analysed to determine the concentration of excipients such as Lactose.

Figure 10:
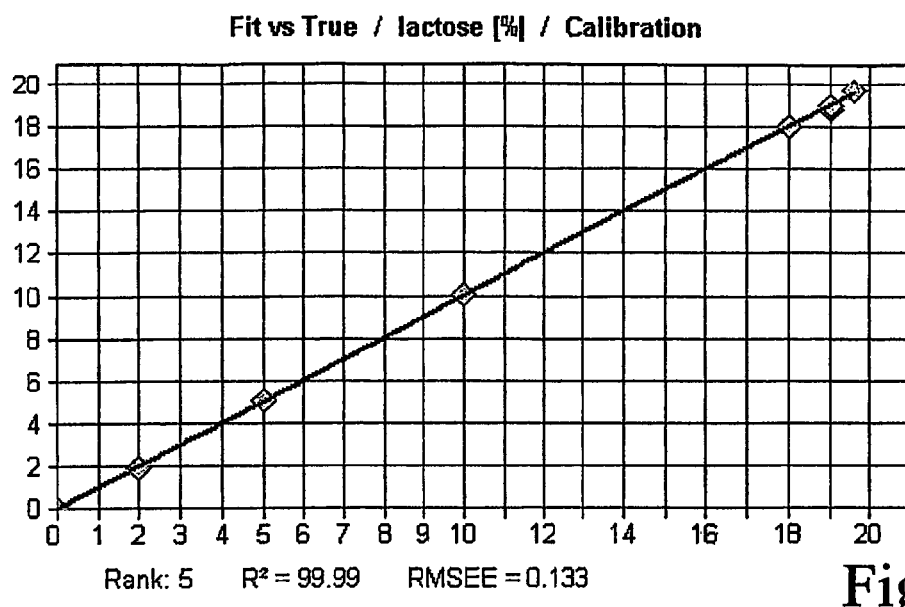
FIG. 10 is a plot of calibration data from a chemometrics analysis package for the excipient lactose derived from a plurality of samples of lactose of known concentration.
Figure 11:
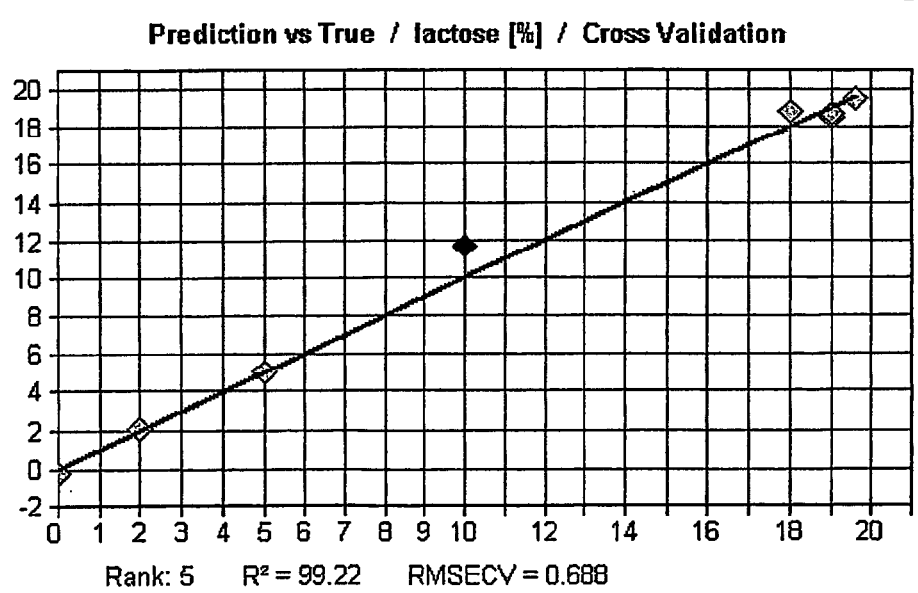
FIG. 11 is a plot showing the validation of the calibration plot of FIG. 10.

FIG. 10 is a calibration plot obtained by analysing the lactose spectral features of the spectrum of FIG. 7. FIG. 11 is a plot showing the validation of the calibration plot of FIG. 10.

As well as analysing solids, the present invention may also be used to analyse the concentration or presence of liquids in gaseous, solid or other liquid media. Pharmaceuticals often degrade with exposure to water vapour in the air and are hence often sealed in the presence of a desiccant or under nitrogen. If the seal fails then water vapour can penetrate the package.

Figure 12:
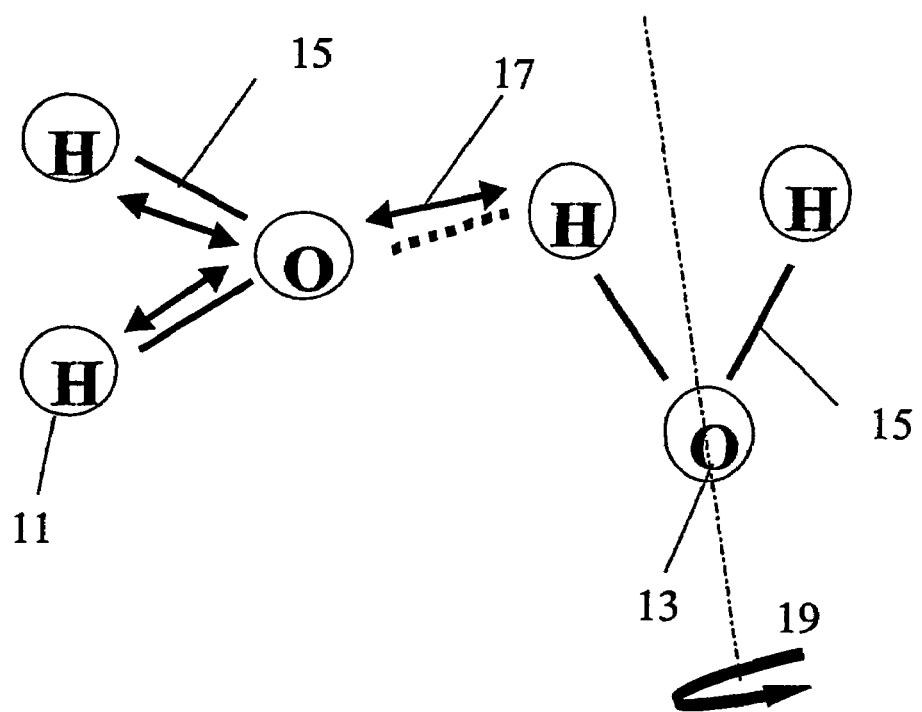
FIG. 12 is a schematic of some possible excitations of two water molecules.

FIG. 12, shows some possible theoretical excitations from a first water molecule 11 and a second water molecule 13.

In FIG. 12, the intra molecular bonds 15 occur between the oxygen and hydrogen atoms of molecules 11 and 13. These bonds generally vibrate at frequencies within the mid infrared range.

Vibrations due to intermolecular interactions are shown as 17, this intermolecular bond is believed to be a hydrogen bond between the two molecules 11 and 13.

One of the possible rotational excitations is shown as 19, the molecule will also rotate about other axis (not indicated).

Both of the above types of non-intramolecular excitations i.e. intermolecular vibrations and rotational excitations are excited at frequencies in the TeraHertz regime.

The spectrum of pure water as a liquid is largely featureless and comprises a gently rising background due to intermolecular vibrations and rotational excitations. In water vapour, the spectrum is dominated by sharp features due to rotational excitations. These are believed to be due to the rotation of free molecules.

To analyse the concentration of water vapour, say for example in a sealed package, features due to rotational excitations are analysed.

Figure 13:
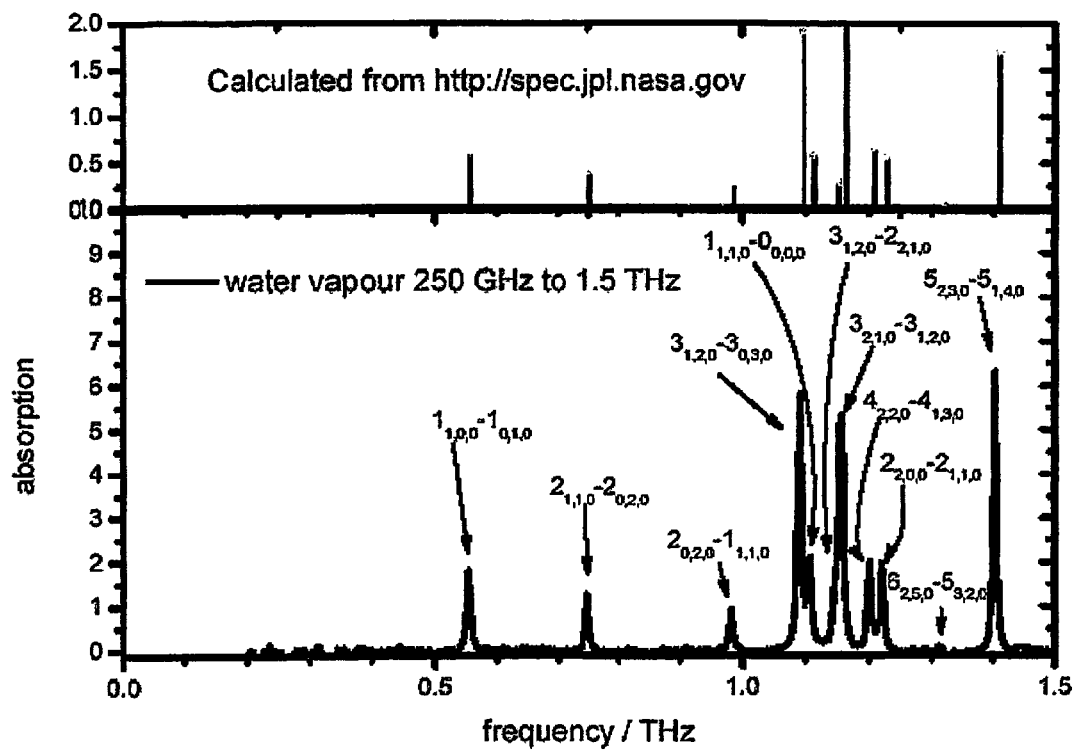
FIG. 13 is a spectrum of absorption against frequency for water vapour.

FIG. 13 is a spectrum of absorption against frequency for water vapour in the range 0.3 to 1.5 THz. Lines of the spectrum have been assigned to various rotational transition using data from the NASA Jet Propulsion Laboratory website at http://spec.jpl.nasa.gov.

A plurality of sample bottles were then prepared. Each sample bottle was prepared at different humidities and then sealed. The humidity during preparation could be fixed by using salt solutions in a well known manner.

The spectrum for each sample was measured using the apparatus of FIG. 1. Two different types of analysis were performed on the spectra in order to derive data for a calibration plot. In the first "model" the second derivative of the spectra between 83 to 75 cm$^{-1}$ (2.5 to 2.3 THz) and 67 to 35 cm$^{-1}$ (2.0 to 1.0 THz) was calculated. In the second model, the base line was subtracted from the spectra by fitting a line through the data points and subtracting it from spectra. The first derivative was then calculated from the base line subtracted data over the range from 74 to 23 cm$^{-1}$ (2.2. to 0.7 THz).

Figure 14:
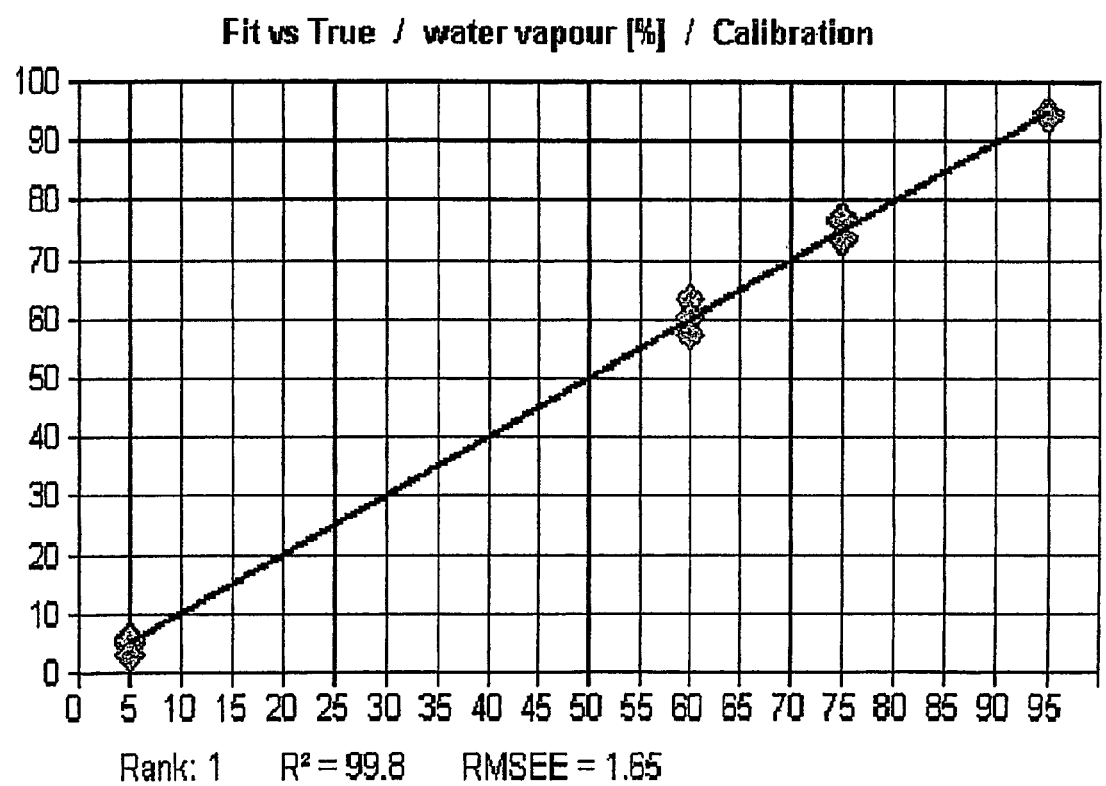
FIG. 14 is a calibration plot derived from sealed samples having known humidities.
Figure 15:
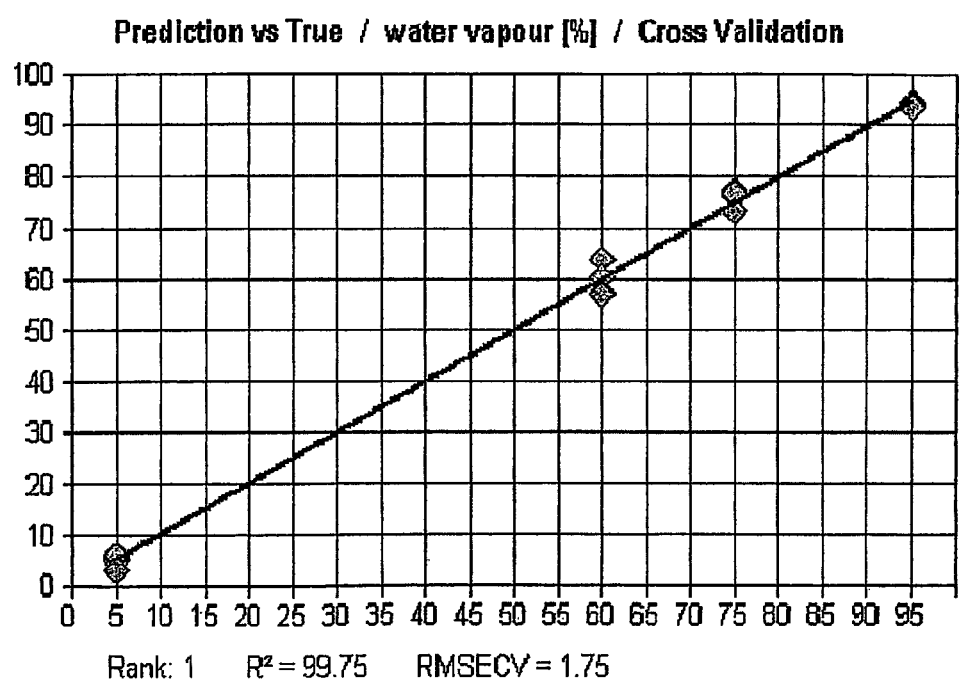
FIG. 15 is a plot showing validation of the calibration data of FIG. 14.

FIG. 14 is a calibration plot derived from sealed samples having known humidities calculated using model 1. FIG. 15 is a plot showing validation of the calibration data of FIG. 14. The validation is achieved by using all but one sample to produce the calibration plot and then using this sample to obtain the cross validation data.

Figure 16:
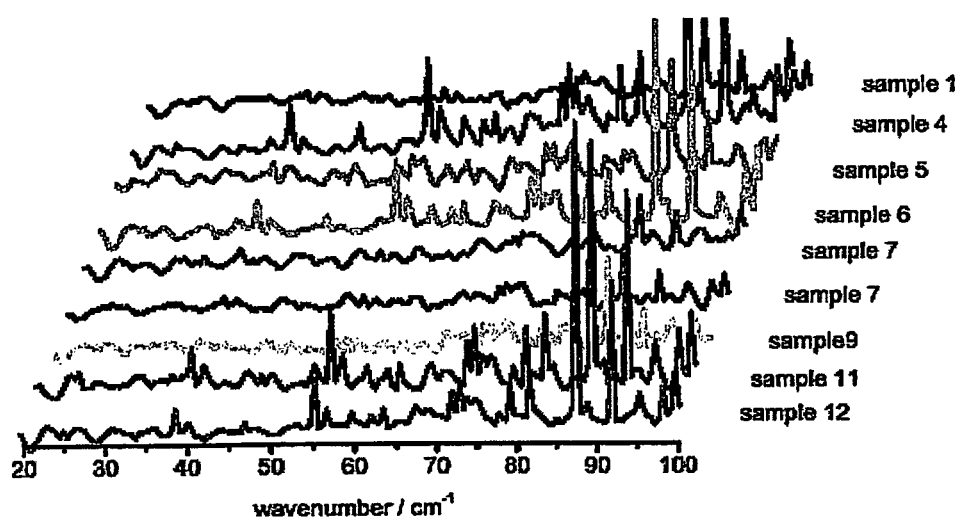
FIG. 16 is a plot of absorption against wavenumber cm$^{-1}$ for a plurality of samples comprising of a sealed bottle containing water vapour.

Then, a further plurality of samples are prepared with differing humidities and with different gases selected from air, oxygen or nitrogen added. The gases were added in order to test that the water content could still be determined in the presence of other gases. A plot of absorption against wavenumber cm$^{-1}$ for the further plurality of samples is shown in FIG. 16.

A chemometric analysis was then performed on each of the spectra using both model 1 and model 2. The value obtained from each spectrum was then plotted on the calibration plot (FIG. 15) in order to obtain the humidity for a given sample.

The results from model 1 and model 2 were averaged to give the data shown in table 1 below:

| Sample Number | Measured Humidity from Chemometric analysis | Actual humidity at 25° C./Environment |
|---|---|---|
| 1 | 23 | 17.3/Air |
| 2 | 60 | 57.9/Air |
| 3 | 43 | 38.4/Air |
| 4 | 67 | 71.5/Air |
| 5 | 38 | 38.4/Nitrogen |
| 6 | 60 | 71.5/Nitrogen |
| 7 | 16 | 17.3/Nitrogen |
| 8 | 53 | 57.9/Nitrogen |
| 9 | 21 | 17.3/Oxygen |
| 10 | 69 | 71.5/Oxygen |
| 11 | 59 | 57.9/Oxygen |
| 12 | 40 | 38.4/Oxygen |

As can be seen from the above results, the method can be used to reliably indicate the amount of water vapour in the bottle regardless of the environment.

The present invention can also be used to measure the amount of vapour due to other molecules as well as water. FIG. 17*a* is a plot of the absorption against frequency for methanol and FIG. 17*b* is a section of the plot of 17*a* enlarged. FIG. 18 is a plot of absorption against frequency for dichloromethane.

FIGS. 19*a* and 19*b* are plots of predicted concentration against actual concentration for acetylsalicyclic acid (aspirin) and Lactose respectively, taken from a plurality of tablets having varying concentrations of aspirin and lactose. Lactose was used as one of the two excipients in the tablets.

The data was derived as previously explained and the first differential of the spectra was taken prior to analysis. In FIG. 19*a*, the RMSECV value is 3.9 and in FIG. 19*b*, the RMSECV value is 4.3.

FIGS. 20*a* and 20*b* are plots of predicted concentration against actual concentration for 4-acetamidophenol (paracetamol) and Lactose respectively, taken from a plurality of tablets having varying concentrations of aspirin and lactose. Lactose was used as one of the two excipients in the tablets.

The data was derived as previously explained and the first differential of the spectra was taken prior to analysis. In FIG. 20*a*, the RMSECV value is 2.85 and in FIG. 20*b*, the RMSECV value is 3.65

The invention claimed is:

1. A method of quantitatively analysing a sample, the method comprising:
    irradiating the sample with radiation having a plurality of frequencies in the range from 25 GHz to 100 THz;
    detecting radiation reflected from and/or transmitted by said sample to obtain a frequency domain waveform of said sample;
    identifying and selecting at least one section of interest of said frequency domain waveform containing spectral features due to intermolecular or other non-intramolecular excitations, wherein the sample has components which are not to be analysed and the at least one section of interest is selected away from strong spectral features which arise from said components not to be analysed; and
    determining the concentration of a component of the sample from the at least one selected section of interest.

2. A method according to claim 1, wherein the sample comprises a molecule which can form at least two polymorphs or psuedo polymorphic states.

3. A method according to claim 2, wherein regions of the spectra where there are differences between the characteristic spectra of the at least two polymorphs or psuedo polymorphic states are identified as sections of interest.

4. A method according to claim 1, wherein said sample comprises two or more components comprising different molecules.

5. A method according to claim 1, wherein the sample comprises an active component and an excipient.

6. A method according to claim 1, wherein the sample comprises solid components.

7. A method according to claim 1, wherein the sample comprises a pharmaceutical.

8. A method according to claim 1, wherein the sample comprises explosive materials.

9. A method according to claim 1, wherein the sample comprises at least one component in the form of a vapour.

10. A method according to claim 9, wherein the vapour is water vapour.

11. A method according to claim 9, wherein the section of interest is chosen as a region of the spectra which contains features arising from rotational excitations of the molecules which comprise the vapour.

12. A method according to claim 1, wherein the sample comprises a sealed package.

13. A method according to claim 12, wherein radiation transmitted by or reflected from the headspace of the package is analysed to determine the vapour content in the package.

14. A method according to claim 1, wherein the sample is analysed through packaging.

15. A method according to claim 1, wherein the sample is irradiated with radiation in the range from 100 GHz to 5 THz.

16. A method according to claim 1, wherein obtaining a value related to the concentration of the component comprises obtaining a derivative of said section.

17. A method according to claim 16, wherein said derivative is the first derivative.

18. A method according to claim 16, wherein said derivative is the second derivative.

19. A method according to claim 1, wherein said step of obtaining a value related to the concentration of a component comprises subtracting a background signal from said detected radiation.

20. A method according to claim 19, wherein said step of subtracting a background signal comprises detecting the radiation reflected from or transmitted by a reference sample placed in the position of the said sample.

21. A method according to claim 19, wherein said step of subtracting a base line signal comprises fitting a straight line to the spectra and subtracting it from said spectra.

22. An apparatus for quantitatively analysing a sample, comprising:
    a source for irradiating the sample with radiation having a plurality of frequencies in the range from 25 GHz to 100 THz;
    a detector for detecting radiation reflected from and/or transmitted by said sample to obtain a frequency domain waveform of said sample;

means for identifying and selecting at least one section of interest of said frequency domain waveform containing spectral features due to intermolecular or other non-intramolecular excitations; and means for determining the concentration of one polymorph of a component of the sample relative to the amount of another polymorph or pseudo polymorph of said component from the at least one selected section of interest.

23. An apparatus according to claim 22, wherein the source is a pulsed source of radiation.

24. An apparatus according to claim 22, wherein the source is a source of continuous wave radiation.

25. An apparatus according to claim 22, wherein the source comprises an optically non-linear member which is configured to output radiation in the desired frequency range in response to irradiation by radiation having two or more different frequencies.

26. An apparatus according to claim 22, wherein the source is comprises a photoconductive antenna which is configured to output radiation in response to a bias applied across the antenna and irradiation by radiation having two or more different frequencies.

27. An apparatus according to claim 22, wherein the source is configured to output radiation in the range from 100 GHz to 5 THz.

28. An apparatus according to claim 22, wherein the detector is configured to detect radiation using electrooptic sampling.

29. An apparatus according to claim 22, wherein the detector comprises a photoconductive antenna.

* * * * *